United States Patent [19]

Walsh

[11] Patent Number: 5,093,018

[45] Date of Patent: * Mar. 3, 1992

[54] DIOXOLANES AND THIO ANALOGS, DERIVATIVES THEREOF AND LUBRICANTS AND FUELS CONTAINING SAME

[75] Inventor: Reed H. Walsh, Mentor, Ohio

[73] Assignee: The Lubrizol Corporation, Wickliffe, Ohio

[ * ] Notice: The portion of the term of this patent subsequent to Dec. 20, 2005 has been disclaimed.

[21] Appl. No.: 488,338

[22] Filed: Mar. 2, 1990

Related U.S. Application Data

[60] Continuation-in-part of Ser. No. 247,028, Sep. 20, 1988, Pat. No. 4,906,253, which is a division of Ser. No. 947,170, Dec. 19, 1986, Pat. No. 4,792,411.

[51] Int. Cl.$^5$ .............. C10M 129/66; C10M 135/34; C10M 135/36

[52] U.S. Cl. .................. 252/47.5; 252/48.6; 252/51.5 R; 252/57

[58] Field of Search ............ 252/47.5, 48.6, 57, 252/51.5 R

[56] References Cited

U.S. PATENT DOCUMENTS

| | | | |
|---|---|---|---|
| 1,837,273 | 12/1931 | Knorr et al. | |
| 2,165,353 | 7/1939 | Dickey | 252/57 |
| 2,421,770 | 6/1947 | Bludworth et al. | 260/338 |
| 2,834,708 | 5/1958 | Riener | 167/30 |
| 3,025,214 | 3/1962 | Eden | 167/33 |
| 3,086,025 | 4/1963 | Tinsley, Jr. | 260/340.9 |
| 3,470,206 | 9/1969 | Martin | 260/327 |
| 3,748,344 | 7/1973 | McCloud et al. | 260/340.7 |
| 3,860,665 | 1/1975 | Beckers | 260/652.5 A |
| 3,862,250 | 1/1975 | Beckers | 260/652.5 R |
| 3,887,628 | 6/1975 | Beckers | 335/363 |
| 3,900,411 | 8/1975 | Andress et al. | 252/52 R |
| 3,900,524 | 8/1975 | Beckers | 260/652.5 R |
| 3,910,845 | 10/1975 | Coon | 252/56 R |
| 3,923,912 | 12/1975 | Beckers | 260/652.5 R |
| 3,996,376 | 12/1976 | Hartmann | 424/278 |
| 4,060,532 | 11/1977 | Hartmann | 260/340 R |
| 4,075,228 | 2/1978 | Gastrock et al. | 260/332.3 P |
| 4,220,561 | 9/1980 | Winter | 252/522 R |
| 4,262,030 | 4/1981 | Winter | 426/535 |
| 4,374,998 | 2/1983 | Boden | 549/430 |
| 4,381,243 | 4/1983 | Boden | 252/8.9 |
| 4,390,345 | 6/1983 | Somorjai | 44/63 |
| 4,390,462 | 6/1983 | Boden | 252/522 R |
| 4,418,231 | 11/1983 | Pamer | 570/115 |
| 4,457,763 | 7/1984 | Siemuth | 44/57 |
| 4,465,869 | 8/1984 | Takaishi et al. | 568/672 |
| 4,501,904 | 2/1985 | Pittet et al. | 549/35 |
| 4,792,411 | 12/1988 | Walsh | 252/47.5 |
| 4,906,253 | 3/1990 | Walsh | 44/63 |

FOREIGN PATENT DOCUMENTS 1131226  6/1958  Fed. Rep. of Germany.
2312963  10/1973  Fed. Rep. of Germany.

OTHER PUBLICATIONS

Chemical Abstracts 106:122644r, Oxygen-containing Fuel Extenders, Spindelbalker, Christian; Schmidt, Alfred.

R. Keskinen et al., Tetrahedron 28, pp. 3943-3955 (1972).

R. C. Elderfield et al., Chapter 1, vol. 5, Heterocyclic Compounds, John Wiley & Sons, Inc., New York (1957).

N. Ogata et al., J. Polymer Science, Polymer Letters Ed. 14, pp. 409-412 (1976).

J. Radell et al., J. Chem. Eng. Data, 16, pp. 104-106 (1971).

M. F. Semmelhack et al., J. Am. Chem. Soc., 95, pp. 7325-7336 (1973).

*Primary Examiner*—Prince Willis, Jr.
*Assistant Examiner*—Jerry D. Johnson
*Attorney, Agent, or Firm*—Joseph P. Fischer; James L. Cordek; Frederick D. Hunter

[57] ABSTRACT

Dioxolanes, thio analogs thereof, and derivatives of these and methods of preparation are described. These materials are useful as additives in lubricants and fuels. Methods for reducing fuel consumption in internal combustion engines employing the lubricating compositions are described.

12 Claims, No Drawings

DIOXOLANES AND THIO ANALOGS, DERIVATIVES THEREOF AND LUBRICANTS AND FUELS CONTAINING SAME

FIELD OF THE INVENTION

This is a continuation-in-part of copending application Ser. No. 07/247,028 filed on Sept. 20, 1988 now U.S. Pat. No. 4,906,253 which is a divisional of application Ser. No. 06/947,170 filed on Dec. 19, 1986 now U.S. Pat. No. 4,792,411, the disclosures of which are hereby incorporated by reference.

This invention relates to lubricating oil and fuel compositions and additives therefor. More particularly, this invention relates to lubricating oil and fuel compositions containing 1,3-dioxolanes, thio analogs and certain derivatives thereof. This invention also relates to methods of improving the operation of mechanical devices and machinery, in particular, methods for reducing the energy required to operate such machinery or mechanical devices, and more particularly, methods for reducing the amount of fuel consumed by internal combustion engines. This invention also relates to certain derivatives of 1,3-dioxolanes and thio analogs thereof, as well as methods for preparing these compounds.

BACKGROUND OF THE INVENTION

Over the years, work has continued to develop improved lubricants and fuels. More recently, there have been numerous efforts directed toward reducing the energy required to operate machinery and other mechanical devices. An area receiving particular notice has been efforts directly toward reducing fuel consumption of internal combustion engines. These efforts have been spurred on by petroleum shortages, the increased cost of energy and the desire for conservation of natural resources. Although recent increases in the availability of petroleum products along with a corresponding reduction in cost have lessened the urgency to improve fuel efficiency, it is reasonably certain that these conditions are only temporary. It is recognized that a situation where energy requirements are reduced is desirable, both because of the conservation factor and because such a situation is economical for the user of the machinery or mechanical device.

Many of the proposed solutions to the problem of reducing energy requirements have been mechanical, as for example, designing equipment to operate more efficiently, building smaller cars and smaller engines and adjusting engines to use a leaner fuel mixture. Other efforts have related to developing lubricants that reduce the overall friction of the engine thereby reducing energy requirements. Some synthetic lubricants have been developed and compounded for use in the automobile engine to reduce fuel consumption. A considerable amount of effort has been expended toward developing additives for use in mineral lubricating oils and greases to reduce the friction property of the oils and greases.

1,3-dioxolanes and their thio analogs are known, as are numerous derivatives thereof. They have been known for many years as flavorings and aroma-enhancing agents.

For example, see U.S. Pat. Nos. 1,837,273; 4,262,030; 2,421,770; 3,748,344. 1,3-dioxolane has been mentioned as a stabilizer for chlorinated solvents. See, for example, U.S. Pat. Nos. 3,860,665; 3,862,250; 3,887,628; and others. U.S. Pat. No. 3,470,206 teaches that organic ethers and thioethers are useful in organic synthesis and may be used in other applications such as lubricating oil additives, ore flotation agents, pesticides for the destruction of houseflies, etc. Succinic derivatives are described as useful in lubricants and/or fuels. See, for example, U.S. Pat. Nos. 3,900,411 and 3,910,845. Cyano-substituted heterocyclic compounds are described as hydraulic fluids in Australian patent specification AU548,921 (Chemical Abstracts 105:100247r). U.S. Patent 4,390,345 teaches 1,3-dioxolane and $C_{1-4}$ substituted derivatives are useful in gasolines containing manganese anti-knock additives. Nitro derivatives are taught in U.S. Pat. No. 4,457,763 as cetane improvers for diesel fuels.

Efforts are continuing in the industry to discover or develop new and improved additives for lubricants and fuels. In particular, materials which provide added performance benefits over prior art materials are of particular interest. In particular, additives which provide fuel-consumption reducing properties are of interest, particularly if the additives do not detract from some other performance characteristic. Multi-functional additives, i.e., those that provide more than one benefit, are of particular interest.

To the extent the references cited hereinabove and in the text that appears hereinafter are applicable to the present invention, they are hereby incorporated by reference herein for such disclosures.

SUMMARY OF THE INVENTION

Lubricating oil and fuel compositions containing as additives 1,3-dioxolanes and thio analogs of 1,3-dioxolanes and certain derivatives thereof are provided in accordance with the present invention. These additives provide a broad spectrum of benefits to the compositions containing them. For example, increased oxidation resistance, cleanliness, friction modification and fuel economy benefits can be realized using the lubricating oils and fuel compositions of this invention. Broadly stated, the present invention contemplates a lubricating oil composition comprising a major amount of an oil of lubricating viscosity and a minor amount of an oil soluble or dispersible compound of the formula:

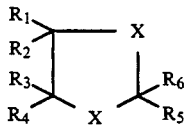
(I)

wherein each X is independently oxygen or sulfur, at least one of the substituents $R_1$-$R_6$ is a member of the group consisting of

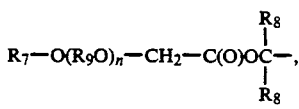
C)

$R_7-O-(R_9O)_n-C(O)-$, and
D)

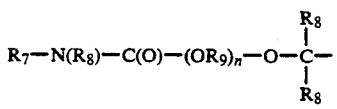
E)

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer from 1 to about 30, and the remaining substituents are independently hydrogen or hydrocarbyl.

This invention also contemplates a fuel composition comprising a major amount of a normally liquid fuel and a minor amount of a compound of the formula:

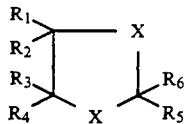 (I)

wherein each X is independently oxygen or sulfur and the substituents $R_1$-$R_6$ are each independently a member of the group consisting of A) hydrogen, B) hydrocarbyl, C) 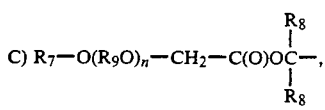

D) $R_7$—O—$(R_9O)_n$—C(O)—, and

E) 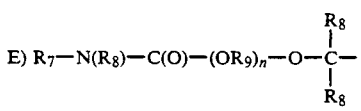

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer from 0 to about 30, with the proviso that at least one of $R_1$-$R_6$ is not hydrogen or hydrocarbyl.

In another embodiment, the fuel composition comprises a compound of formula (I) wherein at least one X is sulfur and the other X is oxygen or sulfur, and the substituents $R_1$-$R_6$ are each independently a member of the group consisting of A) hydrogen, B) hydrocarbyl, C) 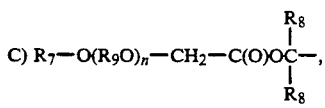

D) $R_7$—O—$(R_9O)_n$—C(O)—, and

E) 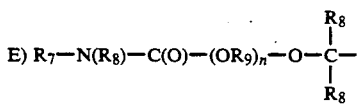

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer from 0 to about 30.

In each of the above-described fuel compositions it is preferred that at least one of $R_1$-$R_4$ is a group other than hydrogen. Preferably, at least one of $R_1$-$R_4$ is a group of formula C), D) or E), as described hereinabove. In another preferred embodiment, within the scope of the definitions hereinabove, at least one of $R_1$-$R_4$ is a hydrocarbyl group, preferably an alkyl or an alkylene group, containing at least 8 carbons, more preferably from about 12 to about 24 carbons, and $R_5$-$R_6$ are both hydrogen or both methyl.

Also provided by this invention is a compound of the formula:

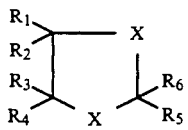 (I)

wherein each X is independently oxygen or sulfur and at least one of the substituents $R_1$-$R_6$ is a group of the formula:

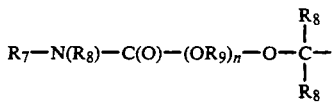 (II)

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer of from 1 to about 30, and the members of $R_1$-$R_6$ that are not groups of formula (II) are each independently hydrogen or hydrocarbyl.

Preferably at least one X is oxygen, more preferably both X are oxygen. In a preferred embodiment $R_7$ is an alkyl or alkenyl group of from about 4 to about 28 carbons, often at least about 8 carbons and preferably from about 12 to about 24 carbons.

In another embodiment, one member of is a group of formula (II) wherein $R_7$ is as defined hereinabove, $R_5$ and $R_6$ are independently hydrogen or hydrocarbyl, and the remaining members of $R_1$-$R_4$ are each independently hydrogen or hydrocarbyl, and $R_8$ is hydrogen. In an especially preferred embodiment only one member of $R_1$-$R_4$ is a group of formula (II) wherein $R_7$ is as defined hereinabove, $R_5$ and $R_6$ are both hydrogen or both methyl, the remaining members of $R_1$-$R_4$ are hydrogen and $R_8$ is hydrogen.

This invention also contemplates a method for preparing a compound of the formula:

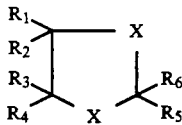 (I)

wherein each X is independently oxygen or sulfur and at least one of the substituents $R_1$-$R_6$ is a group of the formula:

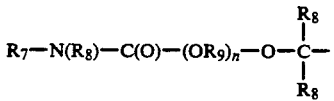 (II)

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer of from 1 to about 30, and the members of $R_1$-$R_6$ that are not groups of formula (II) are each independently hydrogen or hydrocarbyl, which method comprises reacting at least one isocyanate of the formula:

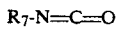

with a compound of the formula:

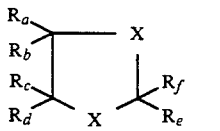
(III)

wherein X is as defined hereinabove, wherein at least one member of $R_a$–$R_f$ is a group of the formula:

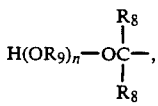
(V)

$R_9$ is an alkylene group having from 2 to about 16 carbons, preferably 2 or 3 carbons, n is an integer from 1 to about 30, and the remaining groups are hydrogen or hydrocarbyl.

Preferably at least one X is oxygen, more preferably both X are oxygen. In a preferred embodiment $R_7$ is an alkyl or alkenyl group of from about 4 to about 28 carbons, often at least about 8 carbons and preferably from about 12 to about 24 carbons.

In another embodiment, one member of $R_a$–$R_d$ is a group of formula (V), $R_e$ and $R_f$ are independently hydrogen or hydrocarbyl, and the remaining members $R_a$–$R_d$ are each independently hydrogen or hydrocarbyl and $R_8$ is hydrogen. In an especially preferred embodiment, only one member of $R_a$–$R_d$ is a group of formula (V), $R_e$ and $R_f$ are both hydrogen or hydrocarbyl, preferably both hydrogen or both methyl, the remaining members of $R_a$–$R_d$ are hydrogen and $R_8$ is hydrogen.

In each case hereinabove, when at least one pair of R's is hydrocarbyl, one R from each of two adjacent ring carbons, they may together form an additional carbon to carbon bond to form a cyclic nucleus and compound (I) or compound III will have the general formula

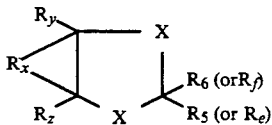

wherein $R_x$ represents the combination of the two R's from the adjacent carbon atoms, and $R_y$ and $R_z$ are each independently hydrogen or hydrocarbyl or, when the combination of the two R's results in the formation of an aromatic ring, $R_y$ and $R_z$ are absent.

Also contemplated by this invention is a method for reducing fuel consumption in an internal combustion engine, which comprises lubricating said engine with the lubricating oil composition described hereinabove and in greater detail hereinbelow.

DETAILED DESCRIPTION OF THE PREFERRED EMBODIMENTS

The Oil of Lubricating Viscosity

The lubricating oil compositions of the present invention comprise a major amount, that is, greater than 50% by weight, of oil of lubricating viscosity, including natural and synthetic lubricating oils and mixtures thereof.

Natural oils include animal oils and vegetable oils (e.g. castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halosubstituted hydrocarbon oils such as polymerized and interpolymerized olefins, etc. and mixtures thereof, alkylbenzenes, polyphenyls (e.g., biphenyls, terphenyls, alkylated polyphenyls, etc.), alkylated diphenyl ethers and ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers or mono- and polycarboxylic esters thereof, for example, the acetic acid esters, mixed $C_3$–$C_8$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, sebacic acid, etc.) with a variety of alcohols (e.g., butyl alcohol, dodecyl alcohol, ethylene glycol, diethylene glycol monoether, etc.)

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants. Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the compositions of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, hydrorefining, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Specific examples of the above-described oils of lubricating viscosity are given in Chamberlin III, U.S. Pat. No. 4,326,972 and European Patent Publication 107,282, both of which are hereby incorporated by reference for relevant disclosures contained therein.

The Compound of Formula (I) in Lubricating Compositions

The lubricating compositions of this invention comprise a minor amount, that is, amounts less than 50% by weight, of an oil soluble or dispersible compound of the formula:

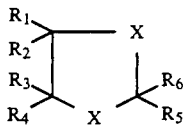

wherein each X is independently oxygen or sulfur, at least one of the substituents $R_1$-$R_6$ is a member of the group consisting of

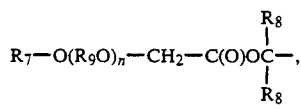 C)

$R_7-O-(R_9O)_n-C(O)-$, and D)

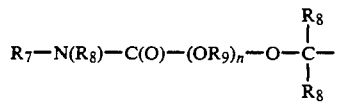 E)

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer from 1 to about 30, and the remaining substituents are independently hydrogen or hydrocarbyl. More often, the lubricating compositions comprise from about 0.1 to about 20%, frequently from about 1 to about 5% by weight of the compound of Formula (I).

Preferably, $R_7$ is an alkyl or alkenyl group having at least about 8 carbon atoms, more preferably from about 12 to about 24 carbon atoms.

In the context of this invention, the word hydrocarbyl is meant to include groups which comprise carbon and hydrogen. Hydrocarbyl groups have a carbon atom directly attached to the remainder of the molecule and have predominantly hydrocarbon character. Such groups are often referred to as hydrocarbon-based groups. Such groups include the following:

(1) Hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, the two indicated substituents may together form a cyclic group). Such groups are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon groups; that is, groups containing non-hydrocarbon substituents which, in the context of this invention, do not alter the predominantly hydrocarbon character of the group. Suitable substituents include halo, hydroxy, alkoxy, carbalkoxy, nitro, alkylsulfoxy and others. These non-hydrocarbon substituents do not include —COOH groups or ester, amide, etc. groups derived therefrom.

(3) Hetero groups; that is, groups which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based group. Most preferably, the hydrocarbon-based groups are purely hydrocarbon.

As mentioned above, each X in formula I is independently sulfur or oxygen. Preferably, at least one X is oxygen. More preferably, both X are oxygen.

Each R, from $R_1$ to $R_6$, in formula I is as defined hereinabove. Within the scope of this definition, particularly preferred is when one of $R_1$-$R_4$ is hydrocarbyl of at least 8 carbon atoms. In this case, it is preferred that the remaining substituents $R_1$-$R_4$ are hydrogen. In this situation especially preferred is wherein $R_5$ and $R_6$ are both hydrogen or both methyl. Particularly preferred is wherein one member of $R_1$-$R_4$ is hydrocarbyl containing at least about 12 carbon atoms, preferably from about 12 to about 24 carbon atoms. Especially preferred is wherein $R_5$ and $R_6$ are both hydrogen or both methyl, one member of $R_1$-$R_4$ is hydrocarbyl from about 12 to about 24 carbon atoms and the remaining unsubstituted portions are hydrogen.

The lubricating compositions of this invention may comprise a compound of formula (I) wherein one of $R_1$ and $R_2$ and one of $R_3$ and $R_4$ is a group of the formula:

wherein $R_9$ is an alkylene group of from 2 to about 16 carbons, preferably 2 or 3 carbons, n is an integer from 1 to about 30, and the other member of each of the stated pairs is hydrogen, and $R_5$ and $R_6$ are both hydrogen or both methyl. Preferably $R_7$ is alkyl or alkenyl having at least about 8 carbon atoms, preferably from about 12 to about 24 carbon atoms.

In each of the above-described cases each X is independently oxygen or sulfur, preferably at least one X is oxygen, more preferably, both X are oxygen.

Methods for preparing many of the compounds of formula (I) are known to one skilled in the chemical arts. For others, methods for preparing such compounds are provided herein.

Martin (U.S. Pat. No. 3,470,206) teaches a method for preparing 1,3-dithiolanes and 1,3-oxathiolanes which involves hydrogenation of organic thiocarbonates.

Gastrock (U.S. Pat. No. 4,075,228) teaches methods for preparing certain substituted 1,3-dithiolanes.

Jones, et al (U.S. Pat. No. 2,701,253) teaches substituted 1,3-dithiolanes made by reacting a dimercaptan with an aromatic aldehyde or ketone.

Jones, et al (U.S. Pat. No. 2,690,988) teaches the reaction of ethylene dimercaptan with aldehydes or ketones, said aldehydes or ketones selected to correspond to the desired substituents on the product.

Riemer (U.S. Pat. No. 2,834,708) teaches the preparation of benzyl substituted 1,3-dioxalanes from 2,2-diphenyl vinyl halides, an alkaline reagent and a glycol.

Eden (U.S. Pat. No. 3,025,214) teaches the preparation of substituted 1,3-oxathiolanes from an aldehyde or ketone and a mercapto alcohol, preferably in the presence of toluene sulfonic acid catalyst.

Tinsley, et al (U.S. Pat. No. 3,086,025) teaches that 1,3-dioxalanes having unsaturated substituents are prepared from the condensation of unsaturated glycols with the appropriate aldehyde or ketone.

Numerous oxathiolanes are described and a general procedure for the preparation of oxathiolanes is given in Winter (U.S. Pat. No. 4,262,030).

Knorr (U.S. Pat. No. 1,837,273) teaches certain araliphatic cyclic acetals prepared by reacting an araliphatic aldehyde with dihydroxy compounds.

Kurosawa, et al ("Tetrahedron Letters", 22, 2121 (1972) describes several 4,5-substituted 1,3-dioxolanes derived from an alga. These materials are also described by the same authors in "Tetrahedron Letters" 1, 3 (1972).

Meskens in "Synthesis", 7, 501 (191) teaches methods for the preparation of acetals from alcohols and carbonyl compounds.

In the "Journal of Polymer Science", 14, 409 (1976) the preparation of the ethyl ester of methylene tartrate from the reaction of ethyl tartrate with dioxane is described.

Radell, et al in "The Journal of Chemical and Engineering Data", 16, 104 (1971) describes the preparation of several 1,3-dioxolanes by alcoholysis of 2,2-dimethoxy-propane.

DE3,110,782 (Kao Soap) - Derwent Abstract 88194D/48 describes 4-alkoxymethyl-1,3-dioxolanes.

The following patents and publications also describe compounds of formula (I) and methods for preparing same:
U.S. Pat. No. 2,421,770 (Bludworth, et al)
U.S. Pat. No. 3,325,406 (Brannen, et al)
U.S. Pat. No. 3,748,344 (McCloud, et al)
U.S. Pat. No. 3,900,411 (Andress, et al)
U.S. Pat. No. 3,910,845 (Coon)
U.S. Pat. No. 4,374,998 (Boden)
U.S. Pat. No. 4,390,345 (Somorjai)
U.S. Pat. No. 4,501,904 (Pillet, et al)
Semmelhack, et al, "Journal of the American Chemical Society" 95, 7325 (1973)
Keskinen, et al, "Tetrahedron" 28, 3943 (1972) Elderfield (Editor), "Heterocylic Compounds", volume 5, John Wiley and Sons (1957)
Breslow and Scolnik in "Heterocylic Compounds" in part I of the volumes entitled Multi-sulfur and Sulfur and Oxygen 5- and 6-membered Heterocycles, Chapters 4 and 5, Interscience Publishers (1966)

Each of the above-mentioned patents and publications is hereby incorporated herein by reference for relevant disclosures contained therein.

Also provided by this invention is a compound of the formula:

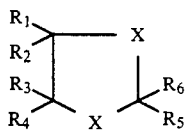

(I)

wherein each X is independently oxygen or sulfur and at least one of the substituents $R_1$-$R_6$ is a group of the formula:

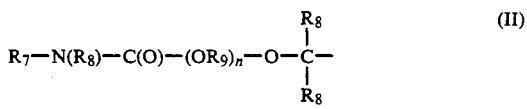

(II)

wherein $R_7$ is hydrocarbyl, each $R_8$ is independently hydrogen or hydrocarbyl, $R_9$ is an alkylene group having from 2 to about 16 carbons, preferably 2 or 3 carbons, and n is an integer of from 1 to about 30, and the members of $R_1$-$R_6$ that are not groups of formula (II) are each independently hydrogen or hydrocarbyl.

Preferably at least one X is oxygen, more preferably both X are oxygen. In a preferred embodiment $R_7$ is an alkyl or alkenyl group of from about 4 to about 28 carbons, often at least about 8 carbons and preferably from about 12 to about 24 carbons.

In another embodiment, one member of $R_1$-$R_4$ is a group of formula (II) wherein $R_7$ is as defined hereinabove, $R_5$ and $R_6$ are independently hydrogen or hydrocarbyl, and the remaining members of $R_1$-$R_4$ are each independently hydrogen or hydrocarbyl, and $R_8$ is hydrogen. In an especially preferred embodiment only one member of $R_1$-$R_4$ is a group of formula (II) wherein $R_7$ is as defined hereinabove, $R_5$ and $R_6$ are both hydrogen or both methyl, the remaining members of $R_1$-$R_4$ are hydrogen and $R_8$ is hydrogen.

Such compounds are prepared by a method which comprises reacting at least one isocyanate of the formula:

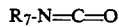

with a compound of the formula:

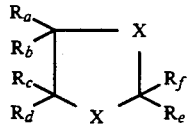

(III)

wherein X is as defined hereinabove, wherein at least one member of $R_a$-$R_f$ is a group of the formula:

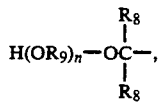

(V)

wherein each of $R_8$, $R_9$ and n is as described hereinabove, and the remaining groups are hydrogen or hydrocarbyl.

Preferably at least one X is oxygen, more preferably both X are oxygen. In a preferred embodiment $R_7$ is an alkyl or alkenyl group of from about 4 to about 28 carbons, often at least about 8 carbons and preferably from about 12 to about 24 carbons.

In another embodiment, one member of $R_a$–$R_d$ is a group of formula (V), $R_e$ and $R_f$ are independently hydrogen or hydrocarbyl, and the remaining members $R_a$–$R_d$ are each independently hydrogen or hydrocarbyl and $R_8$ is hydrogen. In an especially preferred embodiment, only one member of $R_a$–$R_d$ is a group of formula (V), $R_e$ and $R_f$ are both hydrogen or hydrocarbyl, preferably both hydrogen or both methyl, the remaining members of $R_a$–$R_d$ are hydrogen and $R_8$ is hydrogen.

Isocyanates of the formula $R_7N\!\!=\!\!C\!\!=\!\!O$ are well known in the chemical arts and are often commercially available.

Compounds of formula (III) are also well known, as are methods for preparing them. In general, such compounds can be prepared by methods enumerated hereinabove for the preparation of the dioxolanes and derivatives thereof used in the lubricating compositions of this invention. For example, solketal, 2,2-dimethyl-1,3-dioxolane-4-methanol is prepared from the condensation of acetone with glycerine. Other examples of reactant III can be prepared by the above-described methods wherein the reactants employed are selected to provide desired substituents.

As mentioned hereinabove, this invention also contemplates fuel compositions containing certain derivatives of 1,3-dioxolanes and thio analogs thereof.

The following examples are non-limiting illustrations of materials useful in the compositions of this invention.

EXAMPLE 1

A 12-liter flask equipped with a stirrer, a condenser, a thermowell and an addition funnel is charged with 3712 parts acetone and 128.5 parts $AlCl_3$. 1920 parts $C_{16a}$-olefin epoxide is added dropwise from an addition funnel. A slight exotherm is noted. The reaction mixture is heated to 60° C. and held there for 5 hours. Following the heating period, 1600 milliliters of 15% aqueous NaOH is added and the mixture is stirred for 1 hour. The reaction materials are allowed to separate overnight at room temperature. The organic layer is decanted and stripped to 178° C. at 15 millimeters mercury. The residue after stripping is filtered through a diatomaceous earth filter aid yielding 1986 parts of substituted dioxolane.

EXAMPLE 2

The procedure of Example 1 is repeated except 3062 parts of acetone and 270.5 parts $SnCl_4$ are employed. $AlCl_3$ is not used.

EXAMPLE 3

A 1-liter flask equipped with stirrer, condenser and thermowell is charged with 232 parts acetone and 9.7 parts $FeCl_3$. To this mixture is added 120 parts $C_{16a}$-olefin epoxide dropwise from an addition funnel over 1 hour. The mixture is heated to 60° C. and held at 60° C. for a total of 6 hours. 10% aqueous NaOH solution (200 milliliters) is added, the mixture is mixed thoroughly, then allowed to settle. The organic layer is separated, diluted with toluene and washed with two 200 milliliter increments of water. The washed residue is stripped to yield the substituted dioxolane.

EXAMPLE 4

To a 1-liter flask equipped with a stirrer, thermowell, condenser and addition funnel, and containing 34 parts of $SnCl_4$ and 150 milliliters $CCl_4$ is added 384 parts acetone. To this mixture is added 174 parts of $C_{10a}$-olefin epoxide (Vikolox 10 obtained from Viking Chemical Company) dropwise over 45 minutes. The reaction mixture is heated to 60° C. and held at 60° C. for 5 hours. 200 milliliters of 10% NaOH solution is added, the mixture is stirred, then the mixture is allowed to settle. The aqueous layer is drained off and discarded. The organic layer is washed with two 200 milliliter increments of water. The washed organic residue is stripped in vacuo yielding the substituted dioxolane.

EXAMPLE 5

A 2-liter flask equipped with stirrer, condenser, water trap and nitrogen inlet tube is charged with 885 parts of a $C_{15-18}$ vicinal glycol (Adol 158), 90 parts para-formaldehyde and 5.7 parts para-toluene sulfonic acid monohydrate. The mixture is stirred and heated to reflux while nitrogen blowing at 2 cubic feet per hour until 55 parts (54 parts theory) water is collected. The reaction mixture is stripped to 160° C. at 18 millimeters mercury and filtered employing a diatomaceous earth filter aid. The filtrate is the desired product.

EXAMPLE 6

A 5-liter flask equipped with a stirrer, condenser and thermowell is charged with 1475 parts $C_{15-18}$ vicinal glycol (Adol 158), 2000 parts acetone, 52 parts 2,2-dimethoxypropane and 2 parts concentrated $H_2SO_4$. The mixture is heated to reflux and held at reflux for 26 hours. $Na_2CO_3$ (21.2 parts) is added and the mixture is stirred for 3 hours, stripped to 100° C. at 12 millimeters mercury, and filtered using a diatomaceous earth filter aid. The desired product is obtained.

EXAMPLE 7

A reaction flask is charged with 295 parts of $C_{15-18}$ vicinal glycol (Adol 158), 182 parts benzophenone and 400 parts xylene. The mixture is heated and stirred followed by addition of 2.95 parts concentrated $H_2SO_4$. The reaction mixture is held at reflux with nitrogen blowing at 2 cubic feet per hour for 5 hours until 17 parts (18 parts theory) water is removed. To the mixture is added 3.2 parts $Na_2CO_3$ to neutralize any acid remaining. The reaction mixture is stripped to 160° C. at 13 millimeters mercury and filtered two times through a diatomaceous filter aid to yield the mixed alkyl and phenyl substituted dioxolane.

EXAMPLE 8

A 2-liter flask is charged with 676 parts lauric acid (Neofat 12) and 300 parts glycerine, and the materials are heated to 180° C. with nitrogen blowing at 2 cubic feet per hour. Heating and nitrogen blowing at 180° C. is continued with the removal of water until 58 parts (58 parts theory) water is removed. The reaction product is filtered using a diatomaceous earth filter aid.

A 2-liter flask equipped with a nitrogen inlet, thermowell, condenser and Dean-Stark Trap is charged with 685 parts of the above-described glycerine ester, 725 parts acetone, 1 part concentrated $H_2SO_4$ and 26 parts 2,2-dimethoxypropane. The reaction mixture is heated at reflux (approximately 60° C.) for several days. The reaction mixture is stripped to 130° C. at 35 millimeters mercury. The residue is filtered using a diatomaceous earth filter aid.

EXAMPLE 9

A 2-liter flask equipped with a stirrer, thermowell, nitrogen inlet, Dean-Stark Trap and condenser is charged with 264 parts solketal (2,2-dimethyl-1,3-dioxolane-4-methanol) and 565 parts oleic acid. The temperature is increased to 200° C. followed by dropwise addition of 6.8 parts (n-butyl)$_4$Ti. Butanol and water are removed (a total of 117 parts). The reaction product is filtered using a diatomaceous earth filter aid.

EXAMPLE 10

A tartaric acid ester is prepared by reacting 750 parts tartaric acid with 2200 parts $C_{12-14}$ alcohol (Proctor & Gamble) in the presence of 5 parts para-toluene sulfonic acid. The reaction mixture which also contains 1000 parts toluene is heated to reflux while blowing with nitrogen at 2 cubic feet per hour. Water is removed azeotropically. The residue is stripped to 120° C. at 20 millimeters mercury. 2 parts lime is added, and the materials are stirred for 20 minutes, then filtered hot using a diatomaceous earth filter aid.

A 2-liter flask is charged with 771 parts of the tartrate ester, 49.5 parts para-formaldehyde, 400 parts xylene and 2.9 parts para-toluene sulfonic acid monohydrate. The reaction mixture is heated to reflux while stirring and nitrogen blowing at 2 cubic feet per hour while removing water as it forms. The reaction mixture is stripped to 145° C. at 12 millimeters mercury and filtered using a diatomaceous earth filter aid.

EXAMPLE 11

A reaction flask is charged with 1745 parts $C_{10}$ vinylidene dimer and 1716 parts hexanes. The mixture is heated to 70° C. followed by gradual addition of a mixture of 1228 parts peracetic acid and 27 parts sodium acetate, while keeping the temperature between 70°–75° C. The reaction mixture is held at 70° C. for 2 hours, poured into 9 liters water, mixed thoroughly and allowed to settle. The organic layer is separated, washed with 3 liters of 1N $Na_2CO_3$ solution, followed by washing with two 6-liter increments of water. The washed organic layer is dried overnight over $MgSO_4$, filtered through a paper filter and stripped of solvent in vacuo.

A 2-liter flask equipped with a thermowell, stirrer, condenser and addition funnel is charged with 150 milliliters $CCl_4$ and 34 parts $SnCl_4$. While stirring, 384 parts acetone is added. 302 parts of the above-described reaction product is added dropwise over hour, the reaction mixture is heated to 60° C. and held at 60° C. for 8 hours. To the reaction mixture is then added 200 milliliters of 10% NaOH solution followed by mixing and separation of the aqueous layer using a separatory funnel. Toluene, 400 milliliters, is added and the solution is washed twice with 200 milliliter increments of water. The washed organic layer is stripped to 198° C. at 25 millimeters mercury and filtered employing a diatomaceous earth filter aid.

EXAMPLE 12

A 2-liter flask is charged with 340 parts methylnonyl ketone (Armak Chemical), 310 parts ethylene glycol, 200 parts xylene and 3.8 parts para-toluene sulfonic acid. The mixture is heated to reflux while nitrogen blowing. While the material is refluxing, water is collected in a Dean-Stark Trap. After 30 parts water is collected (36 parts theory) 0.74 parts calcium hydroxide is added to neutralize the acid. The mixture is stripped to remove xylene and excess ethylene glycol, and the residue is filtered using a diatomaceous earth filter aid.

EXAMPLE 13

The procedure of Example 12 is repeated except the ketone reactant is methylpentadecyl ketone.

EXAMPLE 14

The procedure of Example 12 is repeated except the ketone is methylundecyl ketone.

EXAMPLE 15

A 2-liter flask equipped with a nitrogen inlet, thermowell, stirrer and condenser is charged with 264 parts solketal and heated to 120° C. 600 parts octadecylisocyanate (Mondur O - Mobay Chemical Corporation) is added dropwise over a 2 hour period while the temperature is held at 120° C. The reaction is followed by infrared analysis, and additional solketal is added dropwise to react with excess isocyanate. After heating for a total of 12 hours, the product is filtered through diatomaceous earth filter aid.

EXAMPLE 16

A reactor is charged with 480 parts $C_{16}$ epoxide, 1.8 liters butanol and 32 parts diethylamine. Hydrogen sulfide is added at 30°–46° C. until a total of 106 parts has been added over 2 hours. The reaction mixture is stripped at 60° C., and 1.8 millimeters mercury over 4 hours.

A 1-liter flask is charged with 180 parts of the above-described reaction product, 206 parts acetone, 7 parts 2,2-dimethoxypropane and 0.3 parts concentrated $H_2SO_4$. The mixture is stirred at reflux for 36 hours, followed by addition of $Na_2CO_3$ and continued stirring at reflux for 0.5 hours. Solvent is removed on a rotary evaporator, and the residue is filtered employing a diatomaceous earth filter aid.

EXAMPLE 17

The second part of the process of Example 16 is repeated except the epoxide/$H_2S$ reaction product is replaced with a $C_{16}$ vicinal dithiol.

EXAMPLE 18

To a suitable reactor is charged 577 parts of Sandopan DTC linear acid (SANDOZ, Atlanta, Ga.) and 100 parts xylene. Heat to reflux to dry azeotropically, then remove xylene. Add 132 parts of Solketal (acetone ketal of glycerine) and 2 parts tetrabutyltitanate. Heat to 180° C. and hold for 6 hours while removing water and butanol. Filter the residue through diatomaceous earth filter aid.

EXAMPLE 19

A two-liter flask is charged with 1050 parts of ethoxylated fatty alcohol (Alfol 1412-60, Conoco Chemicals Company, Houston, Tex.), 150 parts tartaric acid, 2 parts p-toluene sulfonic acid monohydrate, and 300 parts xylene. The reaction mixture is heated to reflux while nitrogen blowing at 2 cubic feet per hour. 35 parts water is collected over 6 hours. 0.9 parts of lime is added, the mixture is stirred for 20 minutes, then the materials are stripped to 120° C. at 20 Torr. The materials are filtered through diatomaceous earth filter aid providing a tartrate ester intermediate.

To a suitable reactor is charged 933 parts of the tartrate ester described hereinabove, 26 parts of paraformaldehyde, 1.5 parts p-tolune sulfonic acid monohydrate and 200 parts xylene. Heat to reflux while blowing with nitrogen at 2 cubic feet per hour, removing water that forms. The materials are then stripped to 145° C. at 12 Torr and filtered through a diatomaceous earth filter aid.

EXAMPLE 20

A one-liter flask equipped with a sparge tube, stirrer and dry ice condenser is charged with 264 parts of Soketal and 1 part sodium metal. The materials are heated to melt the sodium, then the temperature is increased to 170° C. Ethylene oxide is sparged through the mixture at 0.75 moles per hour. The mixture is then heated for an additional 3 hours. The apparatus is capped with a drying tube and cooled overnight. The materials are heated to 170° C. and sparged with ethylene oxide at 0.25 moles per hour for 4 hours, followed by heating for an additional 3 hours. The materials are filtered to provide an ethyoxylated intermediate.

A suitable round-bottomed flask is charged with 380 parts of the above-described ethoxylated product followed by heating to 90° C. Octadecylisocyanate (Mondur O, Mobay), 300 parts is added dropwise over 0.25 hours. The temperature is increased to 140° C. and held at 140° C. for 4 hours. The materials are then filtered through diatomaceous earth filter aid.

EXAMPLE 21

Dissolve 74 parts acetol (hydroxyacetone) in 200 ml. dichloromethane, then add 78 parts 2-mercaptoethanol in a 500 ml. round-bottomed flask fitted with a stirrer, addition funnel, and condenser. Add boron trifluoride etherate catalyst and stir 2 hours. Catalyst is neutralized with a small amount of diethylamine. The reaction mixture is then stripped to remove solvent, and the residue is filtered through diatomaceous earth to give a 1,3-oxathiolane.

76 parts of the 1,3-oxathiolane and 289 parts of azeotropically dried Sandopan DTC linear acid are added to a suitable reactor. With mixing, 0.5 parts of tetrabutyltitanate is added, the mixture is heated to 200° C. and held at 200° C. for 5 hours while removing water and butanol. The materials are then filtered through a diatomaceous earth filter aid.

EXAMPLE 22

A round-bottomed flask is charged with 81 parts of ethyl 1,3-dithiane-2-carboxylate (Aldrich Chemical Company) and 462 parts of Alfol 1412-60 (ethoxylated synthetic linear primary alcohol from Conoco Chemicals Company, Houston, Tex.). While stirring, 0.75 parts of tetrabutyltitanate is added and the mixture is heated to 200° C. for 5 hours while nitrogen blowing at 2 cubic feet per hour to transesterify. Lighter alcohols (ethanol/butanol) are removed by trap. The materials are filtered through a diatomaceous earth filter aid.

EXAMPLE 23

A round-bottomed flask fitted with a Dry Ice condenser, stirrer and sparge tube is charged with 76 parts of the 1,3-oxathiolane as described in Example 21. The materials are heated to 170° C. followed by sparging with ethylene oxide at 0.5 moles per hour for 2 hours. The materials are then stirred at 170° C. for 5 hours, cooled and filtered through a diatomaceous filter aid providing the ethoxylated oxathiolane.

A reactor is charged with 148 parts of the ethoxylated oxathiolane described hereinabove, and the materials are heated to 90° C. Octadecylisocyanate (Mondur O, Mobay), 270 parts is added dropwise over 0.5 hour. The mixture is heated to 150° C. and held for 4 hours. The materials are then filtered through a diatomaceous earth filter aid.

As mentioned hereinabove, compounds disclosed and/or claimed herein are useful lubrication oil additives. They are normally used in an effective amount to attain the desired improvement, i.e., lubricity, antioxidancy, friction modification, fuel economy improvement, detergency, dispersancy and the like. Usually, they are used at about 0.01 to about 20% by weight of the total weight of the lubricating oil composition, preferably from 0.1 to about 10, more preferably from about 0.3 to about 5% by weight, often from about 0.5 to 5 and frequently 0.5 to 3% by weight of the total weight of the lubricating oil composition.

This invention also contemplates the use of other additives in combination with the lubricating oil compositions of the invention. Such additives include, for example, auxiliary detergents and dispersants of the ash producing and ashless type, auxiliary antioxidants, auxiliary antiwear agents, seal swell agents, pour point depressing agents, viscosity improving agents, extreme pressure agents, friction modifiers, color stabilizers and anti-foam agents. Ashless dispersants and detergents are those that are substantially metal free. Such additional additives are well known in the art and are described in detail in many of the patents and other publications incorporated herein by reference.

The following Table I provides examples of lubricating oil compositions of the instant invention. All amounts are by weight unless indicated otherwise.

TABLE I

| | LUBRICATING COMPOSITIONS | | | | | | | | |
|---|---|---|---|---|---|---|---|---|---|
| | Lubricant Example | | | | | | | | |
| Components | A | B | C | D | E | F | G | H | I |
| Reaction product of ethylene polyamine with polyisobutenyl succinic anhydride | 1.96 | 1.96 | 1.72 | 1.72 | 1.72 | 0.97 | 1.96 | 1.96 | 1.96 |
| Reaction product of polybutenyl succinic anhydride with ethylene polyamine and a polyol | | | | | | 1.16 | | | |
| Styrene-alkylmaleate copolymer-heterocyclic amine reaction product | 2.56 | 2.56 | 2.5 | 2.5 | 2.5 | 1.84 | 2.56 | 2.56 | 2.56 |
| Sulfurized fatty ester-fatty acid-olefin mixture | | | 0.98 | 0.98 | 0.98 | | | | |
| Basic calcium petroleum sulfonate | 0.54 | 0.54 | 0.48 | 0.48 | 0.48 | 0.36 | 0.54 | 0.54 | 0.54 |
| Zinc dithiophosphates | 1.50 | 1.50 | 1.31 | 1.31 | 1.31 | 0.95 | 1.50 | 1.50 | 1.50 |
| Basic sodium petroleum sulfonate | 0.41 | 0.41 | 0.37 | 0.37 | 0.37 | 0.41 | 0.41 | 0.41 | 0.41 |

TABLE I-continued

| Components | \multicolumn{9}{c}{LUBRICATING COMPOSITIONS Lubricant Example} | | | | | | | | |
| --- | --- | --- | --- | --- | --- | --- | --- | --- | --- |
| | A | B | C | D | E | F | G | H | I |
| Basic magnesium alkyl salicylate | | | | | 0.23 | | | | |
| Alkylated aryl amine | | | | | 0.17 | | | | |
| Sulfurized Diels-Alder adduct | | | | | 0.40 | | | | |
| Silicone anti-foam | 9 ppm | 9 ppm | 9 ppm | 9 ppm | 9 ppm | 5 ppm | 9 ppm | 9 ppm | 9 ppm |
| Product of Example 1 | 1 | | | | | | | | |
| Product of Example 3 | | 1 | | | | | | | |
| Product of Example 5 | | | 3.3 | | | | | | |
| Product of Example 6 | | | | 3.3 | | | | | |
| Product of Example 8 | | | | | 1 | | | | |
| Product of Example 10 | | | | | | 1 | | | |
| Product of Example 12 | | | | | | | 1 | | |
| Product of Example 15 | | | | | | | | 1 | |
| Product of Example 17 | | | | | | | | | 1 |

The Normally Liquid Fuel

The fuels which are contemplated for use in the fuel compositions of the present invention are normally liquid hydrocarbon fuels in the gasoline boiling range, including hydrocarbon base fuels. The term "petroleum distillate fuel" also is used to describe the fuels which can be utilized in the fuel compositions of the present invention and which have the above characteristic boiling points. The term, however, is not intended to be restricted to straight-run distillate fractions. The distillate fuel can be straight-run distillate fuel, catalytically or thermally cracked (including hydro cracked) distillate fuel, or a mixture of straight-run distillate fuel, naphthas and the like with cracked distillate stocks. The hydrocarbon fuels also can contain non-hydrocarbonaceous materials such as alcohols, ethers, organo-nitro compounds, etc. Such materials can be mixed with the hydrocarbon fuel in varying amounts of up to about 10–20% or more. For example, alcohols such as methanol, ethanol, propanol and butanol, and mixtures of such alcohols are included in commercial fuels in amounts of up to about 10%. Other examples of materials which can be mixed with the fuels include diethyl ether, methyl ethyl ether, methyl tertiary butyl ether, and nitromethane. Also included within the scope of the invention are liquid fuels derived from vegetable or mineral sources such as corn, alfalfa, shale and coal. Also, the base fuels used in the formation of the fuel compositions of the present invention can be treated in accordance with well-known commercial methods, such as acid or caustic treatment, hydrogenation, solvent refining, clay treatment, etc.

Gasolines are supplied in a number of different grades depending on the type of service for which they are intended. The gasolines utilized in the present invention include those designed as motor and aviation gasolines. Motor gasolines include those defined by ASTM specification D-439-73 and are composed of a mixture of various types of hydrocarbons including aromatics, olefins, paraffins, isoparaffins, naphthenes and occasionally diolefins. Motor gasolines normally have a boiling range within the limits of about 21° C.–232° C. (70° F.–450° F.) while aviation gasolines have narrower boiling ranges, usually within the limits of about 37° C.–169° C. (100° F.–330° F.).

The normally liquid fuels also may be essentially non-hydrocarbon materials such as defined hereinabove. Accordingly, the fuels may also be alcohols, preferably lower alcohols such as methanol and ethanol, ethers, organo nitro compounds and the like.

Methods for reducing fuel consumption in an internal combustion engine, which method comprises lubricating said engine with the lubricating oil compositions of this invention are also contemplated. Fuel consumption of internal combustion engines can be measured using tests having a wide range of sophistication. One well-known test is a motored engine friction horsepower test wherein a test engine is motored by a motoring-absorbing dynamometer. Another is a dynamometer fuel consumption test wherein fuel consumption is measured on a dynamometer controlled operating vehicle. Fleet car tests and other tests are also employed.

As mentioned hereinabove, the compounds disclosed and/or claimed herein are also useful as additives for normally liquid fuels. These additives are used at effective levels to obtain the desired property. They are usually used at from about 10 parts per million parts of total fuel composition (ppm) to about 10% by weight. More preferably they are used at from about 10 ppm to about 1%, often from 50 ppm to about 1% and frequently from about 50 ppm to about 500 ppm by weight of the total weight of the fuel composition.

What is claimed is:

1. A lubricating oil composition comprising a major amount of an oil of lubricating viscosity and a minor amount of an oil soluble or dispersible compound of the formula:

(I)

wherein each X is independently oxygen or sulfur, at least one of the substituents $R_1$–$R_6$ is a member of the group consisting of

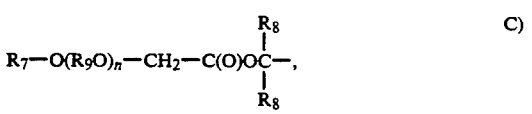

C)

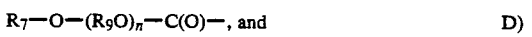

D)

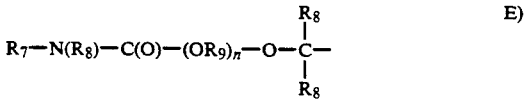

E)

wherein $R_7$ is hydrocarbyl, each $R_8$ is independently hydrogen or hydrocarbyl, $R_9$ is an alkylene group having from 2 to about 16 carbons, and n is an integer from 1 to about 30, and the remaining substituents $R_1$-$R_6$ are independently hydrogen or hydrocarbyl.

2. The composition of claim 1 wherein at least one of X is oxygen.

3. The composition of claim 1 wherein both X are oxygen.

4. The composition of claim 1 wherein at least one of $R_1$-$R_4$ is hydrocarbyl of at least 8 carbon atoms.

5. The composition of claim 4 wherein $R_5$ and $R_6$ are both hydrogen or both methyl.

6. The composition of claim 1 wherein at least one member of $R_1$-$R_4$ is a group of the formula:

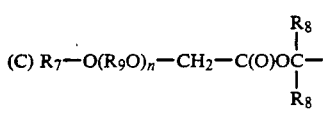

(C) $R_7-O(R_9O)_n-CH_2-C(O)OC-$ wherein $R_7$ is hydrocarbyl, $R_5$ and $R_6$ are both hydrogen or both methyl, n is an integer from 1 to about 30, and $R_9$ is an alkylene group having from 2 to about 16 carbons.

7. The composition of claim 6 wherein $R_7$ is an alkyl or alkenyl group having at least about 8 carbon atoms.

8. The composition of claim 1 wherein one of $R_1$ and $R_2$ and one of $R_3$ and $R_4$ is a group of the formula:

$R_7O$-$(R_9O)_n$-$C(O)$-           (D)

wherein $R_9$ is an alkylene group of from 2 to about 16 carbons, n is an integer from 1 to about 30, and the other member of each of the stated pairs is hydrogen.

9. The composition of claim 8 wherein $R_7$ is alkyl or alkenyl having at least about 8 carbon atoms.

10. The composition of claim 1 wherein at least one member of $R_1$-$R_4$ is a group of the formula:

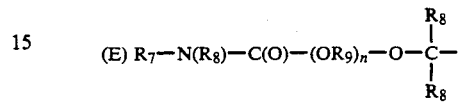

(E) $R_7-N(R_8)-C(O)-(OR_9)_n-O-C-$ wherein $R_9$ and n are as defined hereinabove, wherein $R_7$ is a hydrocarbyl group and each $R_8$ is independently hydrogen or hydrocarbyl, and $R_5$ and $R_6$ are both hydrogen or both methyl.

11. The composition of claim 10 wherein $R_7$ is alkyl or alkenyl having at least 8 carbon atoms and $R_8$ is hydrogen.

12. A method for reducing fuel consumption in an internal combustion engine, which comprises lubricating said engine with the lubricating oil composition of claim 1.